United States Patent [19]

Onishi et al.

[11] Patent Number: 5,439,251

[45] Date of Patent: Aug. 8, 1995

[54] METHOD OF TETRAZOLE AMINE SALTS HAVING IMPROVED PHYSICAL PROPERTIES FOR GENERATING GAS IN AIRBAGS

[75] Inventors: Atsuhiro Onishi; Hiroshi Tanaka, both of Takasago, Japan

[73] Assignee: Toyo Kasei Kogyo Company Limited, Japan

[21] Appl. No.: 158,307

[22] Filed: Nov. 29, 1993

[30] Foreign Application Priority Data

Nov. 30, 1992 [JP] Japan .................. 4-345568

[51] Int. Cl.$^6$ .................. C06B 31/28; C06B 31/02
[52] U.S. Cl. .................. 280/741; 149/61; 149/22; 149/46
[58] Field of Search .................. 548/250; 280/728 R

[56] References Cited

U.S. PATENT DOCUMENTS

| | | | |
|---|---|---|---|
| 3,374,188 | 3/1968 | Marsh et al. | 260/2.5 |
| 3,468,730 | 9/1969 | Gawlick et al. | 149/61 |
| 3,719,604 | 3/1973 | Prior et al. | 352/186 |
| 3,739,574 | 6/1973 | Godfrey et al. | 60/39.03 |
| 3,898,112 | 8/1975 | Strecker et al. | 149/19.9 |
| 4,634,650 | 1/1987 | Suzuki | 430/10 |
| 4,798,637 | 1/1989 | Hendrickson | 45/8 |
| 4,909,549 | 3/1990 | Poole et al. | 280/738 |
| 4,948,439 | 8/1990 | Poole et al. | 149/46 |
| 5,035,757 | 7/1991 | Poole | 149/46 |
| 5,084,118 | 1/1992 | Poole | 149/22 |
| 5,139,588 | 8/1992 | Poole | 149/61 |
| 5,197,758 | 3/1993 | Lund et al. | 280/741 |

Primary Examiner—David B. Springer
Attorney, Agent, or Firm—Wenderoth, Lind & Ponack

[57] ABSTRACT

Tetrazoles of improved physical properties as produced by converting them into their amine salts represented by the following chemical formula (1):

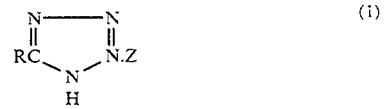

wherein R represents hydrogen, alkyl, phenyl, benzyl or phenethyl group, which may be substituted by an alkyl with carbon number 1-3, chlorine, hydroxyl, carboxyl, methoxy, aceto, nitro or other group, and wherein R may also be tetrazolyl group, which may be substituted via diazo or triazo group, and wherein Z is an amine.

The tetrazole amine salts are useful as gas-generating agents for air-bags or as foaming agents for high polymers.

2 Claims, No Drawings

METHOD OF TETRAZOLE AMINE SALTS HAVING IMPROVED PHYSICAL PROPERTIES FOR GENERATING GAS IN AIRBAGS

(II) BACKGROUND OF THE INVENTION

(1) Field of the Invention

The present invention relates to a method of improving the physical properties of tetrazoles.

Compounds to be employed in the present invention, which are represented by the chemical formula (1) shown later and which have been discovered by the present inventors, can be improved in such physical properties as impact sensitivity and friction sensitivity with respect to conventional tetrazoles. Therefore, they are useful as less-toxic gas-generating agents for air-bags or as foaming agents for high polymers. As such, they are expected to be widely used as safe, easy-to-handle gas-generating agents or foaming agents for high polymers.

(2) Description of the Prior Art

Compounds of free radicals [5,5'-bi-1H-tetrazole (abbreviated as BHT hereinafter)] represented by the chemical formula (1) shown later have been utilized as gas-generating agents for air-bags or as foaming agents for high polymers. When a BHT compound is employed as a gas-generating agent for air-bags, it involves converting the compound into fine powder and loading it into a container for acceleration of its thermal decomposition. In such processes, due to its high impact and friction sensitivities, it may decompose during powdering or explode at the time of loading. When the BHT compound is used as a foaming agent for high polymers, on the other hand, it would be necessary to form master chips by adding the BHT compound to a thermoplastic resin with a melting point somewhat lower than that of the high polymer to be molded so that the BHT compound can be easily added to the polymer and that a preferable dispersion state of the compound into the high polymer to be molded can be obtained.

(III) SUMMARY OF THE INVENTION

In forming the master chips, there has been a problem that because of their poor physical properties tetrazole compounds may often decompose at temperatures lower than the proper decomposition temperature (at the molding temperature of the master chips obtained by adding the compounds to a thermoplastic resin with a melting point somewhat lower than that of the high polymer to be molded), such that desired master chips cannot be obtained.

The object of the present invention is therefore to provide a method of producing tetrazole amine salts of improved physical properties which can be used as gas-generating agents for air-bags or as foaming agents for high polymers, by converting BHT compounds into amine salts.

(IV) DETAILED DESCRIPTION OF THE INVENTION

According to a first aspect of the present invention, there is provided a method of manufacturing tetrazole amine salts of improved physical properties comprising a step of converting the tetrazoles into tetrazole amine salts represented by the following chemical formula (1):

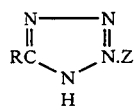

Chemical formula (1)

wherein R represents hydrogen, alkyl, phenyl, benzyl or phenetyl group, which may be substituted by an alkyl with carbon number 1 to 3, chlorine, hydroxyl, carboxyl, methoxy, aceto, amino, nitro or other group, and wherein R may also be tetrazolyl group, which may be substituted via diazo or triazo group.

Z is selected from such primary amines as methylamine, ethylamine, n-propylamine, isopropylamine, n-butylamine, ter-butylamine, n-pentylamine, n-hexylamine, aniline, benzylamine, phenetylamine, 1-amino-4-phenylbutane, benzhydrylamine and cyclohexylamine; from such secondary amines as dimethylamine, diethylamine, di-n-propylamine, di-n-pentylamine, di-n-hexylamine, propyleneimine, pyrrolidine, piperidine and N-methylmorpholine; from such tertiary amines as trimethylamine, triethylamine, tri-n-pentylamine, tri-n-hexylamine, triphenylamine, pyridine and 1,8-diazabicyclo[5,4,0]-7-undecene; from such diamines as hydrazine, trimethylenediamine, pentamethylenediamine, hexamethylenediamine, piperazine, m-phenylenediamine, 1,3-diazacyclohexane, triethylenediamine, N,N,N',N'-tetramethylethylenediamine; and from such compounds as ammonia, urea, carbohydrazide, thiocarbohydrazide, azodicarbonamide, guanidine, dicyandiamide, aminoguanidine, N,N'-bis(3-aminopropyl)piperazine, melamine, acetoguanamine, 3-amino-1,2,4-triazole and hexamethylenetetramine.

According to a second aspect of the present invention, there is provided a method of reducing physical properties of tetrazoles as described for the first aspect, wherein the tetrazole amine salts represented by the above chemical formula (1) are used for air-bags or as foaming agents for high polymers.

(V) EXAMPLES

Example 1

Piperazine salt of 5,5'-bi-1H-tetrazole [Compound (1)]

5,5'-Bi-1H-tetrazole (13.8 g) and piperazine hexahydrate (9.7 g) were added to 200 g of water and the mixture was heated to 80° C. for allowing them to react at this temperature for 1 hour. Then the mixture was cooled to room temperature and filtered to obtain 9.5 g of Compound (1). While 5,5'-bi-1H-tetrazole showed a decomposition temperature of 254° C., a drop hammer sensitivity of JIS class 4 and a friction sensitivity of JIS class 2, Compound (1), namely the piperazine salt of 5,5'-1H-tetrazole, showed a decomposition temperature of 330° C., a drop hammer sensitivity of JIS class 8 and a friction sensitivity of JIS class 7, demonstrating that the objective of the present invention was achieved.

Example 2 m-Phenylenediamine salt of 5,5'-bi-1H-tetrazole [Compound (2)]

5,5'-Bistetrazole (2.7 g) and m-phenylenediamine (2.3 g) were added into 200 g of water and allowed to react at room temperature for 1 hour. Then the solvent was distilled away nearly completely and the residue was filtered to obtain 4.3 g of Compound (2). 5,5'-Bistetrazole showed a decomposition temperature of 254° C., a drop hammer sensitivity of JIS class 4 and a friction sensitivity of JIS class 2, while Compound (2) showed a decomposition temperature of 250° C., a drop hammer sensitivity of JIS class 8 and a friction sensitivity of JIS class 7, thus showing that the objective of the present invention was achieved.

Example 3

Results of thermal analysis and physical properties of various amine salts of 5,5'-bi-1H-tetrazole (abbreviated as BHT) are shown in Table 1.

TABLE 1

Results of Thermal Analysis and Physical Properties of Amine Salts of BHT

| Amines | Mole ratio Amine:BHT | mp °C. | DTA Exothermal peak temperature (°C.) | Friction sensitivity JIS | Drop hammer sensitivity JIS |
|---|---|---|---|---|---|
| (BHT) | | — | 254 | Class 2 | Class 4 |
| Ammonia | 2:1 | 220 | 267 | Class 7 | Class 8 |
| Urea | 1:1 | 186 | 290 | ↑ | ↑ |
| Hydrated hydrazine | 1:1 | 220 | 279 | ↑ | ↑ |
| Hexamethylenediamine | 1:1 | — | 310 | ↑ | ↑ |
| m-Phenylenediamine | 1:1 | 232 | 250 | ↑ | ↑ |
| Melamine | 1:1 | — | 327 | ↑ | ↑ |
| Acetoguanamine | 1:1 | — | 320 | ↑ | ↑ |
| N,N'-Bis(3-aminopropyl)piperazine | 1:1 | 280 | 300 | ↑ | ↑ |
| 3-Amino-1,2,4-triazole | 1:1 | 250 | 278 | ↑ | ↑ |
| Guanidine | 1:1 | 312 | 318 | ↑ | ↑ |
| Aminoguanidine | 1:1 | 240 | 288 | ↑ | ↑ |
| Carbohydrazide | 1:1 | 194 | 280 | ↑ | ↑ |
| Guocarbohydrazide | 1:1 | — | 210 | ↑ | ↑ |
| Azodicarbonamide | 1:1 | — | — | ↑ | ↑ |
| Dicyandiamide | 2:1 | — | 192 | ↑ | ↑ |
| Piperazine | 1:1 | — | 332 | ↑ | ↑ |
| Trimethylamine | 2:1 | 38 | 288 | ↑ | ↑ |
| N,N,N',N'-Tetramethylethylenediamine | 1:1 | — | 296 | ↑ | ↑ |
| Hexamethylenetetramine | 1:1 | — | 285 | ↑ | ↑ |
| Triethylamine | 1:1 | — | 277 | ↑ | ↑ |
| Triphenylamine | 1:1 | 220 | — | ↑ | ↑ |

Note:
( ↑ ) denotes "same as above".

Example 4

Results of thermal analysis and physical properties of various amine salts of 1H-tetrazole (abbreviated as 1HT) are shown in Table 2.

Example 5

Results of thermal analysis and physical properties of various amine salts of 5-methyl-1H-tetrazole (abbreviated as M5T) are shown in Table 3. The results in Table 3 show that M5T has rather low sensitivities and that its conversion to amine salts hardly affects on the physical properties.

Other tetrazole amine salts with other different groups for Z in the chemical formula (1) were also tested to find that they also have been improved in the physical properties of the parent tetrazoles.

(VI) Effect of the Invention

The effect of the present invention may be summarized as follows.

While tetrazoles have been known to be useful as gas-generating agents for air-bags by virtue of their low toxicity of decomposed gases and as foaming agents for high polymers by virtue of their high thermal decomposition temperature, they have been troublesome in use because of their poor physical properties. The present invention has made it possible to overcome the above problems, opening up applications of these compounds in the above discussed fields. The effect of the invention is thus believed to be enormous.

TABLE 2

Results of Thermal Analysis and Physical Properties of Amine Salts of 1HT

| Amines | Mole ratio Amine:1HT | mp °C. | DNA Exothermal peak temperature (°C.) | DSC Exothermal peak temperature (°C.) | Friction sensitivity JIS | Drop hammer sensitivity JIS |
|---|---|---|---|---|---|---|
| (1HT) | | 153 | 231 | 270 | Class 5 | Class 2 |
| n-Propylamine | 1:1 | 209 | — | 248 | Class 7 | Class 8 |
| n-Pentylamine | 1:1 | 205 | — | 260 | ↑ | ↑ |
| Aniline | 1:1 | 225 | — | 248 | ↑ | ↑ |
| Benzylamine | 1:1 | 204 | — | 257 | ↑ | ↑ |
| 1-Amino-4-phenylbutane | 1:1 | 220 | — | 264 | ↑ | ↑ |
| Isopropylamine | 1:1 | 217 | — | 260 | ↑ | ↑ |
| ter-Butylamine | 1:1 | 207 | — | 257 | ↑ | ↑ |
| Benzhydrylamine | 1:1 | 203 | — | 241 | ↑ | ↑ |
| Dimethylamine | 1:1 | 214 | — | 258 | ↑ | ↑ |
| Di-n-propylamine | 1:1 | 209 | — | 256 | ↑ | ↑ |

TABLE 2-continued

Results of Thermal Analysis and Physical Properties of Amine Salts of 1HT

| Amines | Mole ratio Amine:1HT | mp °C. | DNA Exothermal peak temperature (°C.) | DSC Exothermal peak temperature (°C.) | Friction sensitivity JIS | Drop hammer sensitivity JIS |
|---|---|---|---|---|---|---|
| Di-n-pentylamine | 1:1 | 220 | — | 264 | ↑ | ↑ |
| Propyleneimine | 1:1 | — | 222 | 226 | ↑ | ↑ |
| Pyrrolidine | 1:1 | 219 | — | 260 | ↑ | ↑ |
| Piperidine | 1:1 | 219 | — | 258 | ↑ | ↑ |
| Trimethylamine | 1:1 | 204 | — | 253 | ↑ | ↑ |
| Triethylamine | 1:1 | 210 | — | 255 | ↑ | ↑ |
| Tripentylamine | 1:1 | 163 | — | 251 | ↑ | ↑ |
| Trimethylenediamine | 1:1 | 244 | — | 267 | ↑ | ↑ |
| ↑ | 1:2 | 240 | — | 268 | ↑ | ↑ |
| Pentamethylenediamine | 1:1 | 249 | — | 276 | ↑ | ↑ |
| ↑ | 1:2 | 269 | 454 | 276 | ↑ | ↑ |
| Piperazine | 1:1 | 222 | — | 262 | ↑ | ↑ |
| ↑ | 1:2 | 231 | — | 278 | ↑ | ↑ |
| 1,3-Diazacyclohexane | 1:1 | 243 | — | 269 | ↑ | ↑ |
| ↑ | 1:2 | 247 | — | 263 | ↑ | ↑ |
| Triethylenediamine | 1:1 | 243 | — | 225 | ↑ | ↑ |
| ↑ | 1:2 | 221 | — | 258 | ↑ | ↑ |
| Hexamethylenetetramine | 1:1 | 200 | 252 | 258 | | |
| ↑ | 1:2 | 202 | 241 | 260 | | |
| ↑ | 1:3 | — | 187 | 219 | | |
| ↑ | 1:4 | — | 211 | 220 | | |

Note:
( ↑ ) denotes "same as above".

TABLE 3

Results of Thermal Analysis and Physical Properties of Amine Salts of M5T

| Amines | Mixing ratio Amine:M5T | mp °C. | DTA Exothermal peak temperature (°C.) | Friction sensitivity JIS | Drop hammer sensitivity JIS |
|---|---|---|---|---|---|
| (M5T) | | 140 | — | Class 5 | Class 5 |
| Ammonia | 1:1 | 86 | — | Class 7 | Class 8 |
| Methylamine | 1:1 | 90 | — | ↑ | ↑ |
| Ethylamine | 1:1 | ?? | — | ↑ | ↑ |
| Isopropylamine | 1:1 | 58 | — | ↑ | ↑ |
| n-Butylamine | 1:1 | ?? | — | ↑ | ↑ |
| Cyclohexylamine | 1:1 | 130 | — | ↑ | ↑ |
| Aniline | 1:1 | 140 | — | ↑ | ↑ |
| Benzylamine | 1:1 | 90 | — | ↑ | ↑ |
| β-Phenethylamine | 1:1 | 101 | — | ↑ | ↑ |
| Dimethylamine | 1:1 | 90 | — | ↑ | ↑ |
| Diethylamine | 1:1 | 70 | — | ↑ | ↑ |
| Dicyclohexylamine | 1:1 | 150 | — | ↑ | ↑ |
| Piperidine | 1:1 | 100 | — | ↑ | ↑ |
| Piperazine | 1:1 | 91 | — | ↑ | ↑ |
| N-Methylmorpholine | 1:1 | 80 | — | ↑ | ↑ |
| Pyridine | 1:1 | 144 | — | ↑ | ↑ |
| 1,8-Diazabicyclo [5,4,0]-7-undecene | 1:1 | — | — | ↑ | ↑ |
| Triethylamine | 1:1 | — | — | ↑ | ↑ |
| Aminoguanidine | 1:1 | 132 | — | ↑ | ↑ |
| Melamine | 1:1 | — | — | ↑ | ↑ |

Note:
( ↑ ) denotes "same as above".

What we claim is:

1. An airbag assembly which comprises an airbag and, as a gas generating agent therefor, tetrazole amine salts of formula (I)

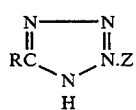

wherein R represents methyl or tetrazolyl, and wherein Z is a member selected from the group consisting of methylamine, ethylamine, n-propylamine, isopropylamine, n-butylamine, tert-butylamine, n-pentylamine, n-hexylamine, aniline, benzylamine, phenethylamine, 1-amino-4-phenylbutane, benzhydrylamine, cyclohexylamine, dimethylamine, diethylamine, di-n-propyl amine, di-n-pentylamine, di-n-hexylamine, propyleneimine, pyrrolidine, piperidine, N-methylmorpholine, trimethylamine, triethylamine, tri-n-pentylamine, tri-n-hexylamine, triphenlyamine, pyridine, 1,8-diazabicyclo-[5,4,0]-7-undecene, hydrazine, trimethylenediamine, pentamethylenediamine, hexamethylenediamine, piperazine, m-phenylendiamine, 1,3-diazocyclohexane, triethylendiamine, N, N, N', N'-tetramethylethylenediamine, ammonia, urea, carbohydrazide, thiocarbohydrazide, azodicarbonamide, guanidine, dicyandiamide, aminoguanidine, N, N'-bis (3-aminopropyl) piperazine, melamine, acetoguanamine, 3-amino-1,2,4-tetrazole and hexamethylenetetramine.

2. A method of generating gas for airbags which comprises employing as the gas generating agent a tetrazole amine salts of formula (I)

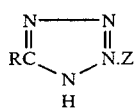 (I)

wherein R represents methyl or tetrazolyl, and wherein Z is a member selected from the group consisting of methylamine, ethylamine, n-propylamine, isopropylamine, n-butylamine, tert-butylamine, n-pentylamine, n-hexylamine, aniline, benzylamine, phenethylamine, 1-amino-4-phenylbutane, benzhydrylamine, cyclohexylamine, dimethylamine, diethylamine, di-n-propyl amine, di-n-pentylamine, di-n-hexylamine, propyleneimine, pyrrolidine, piperidine, N-methylmorpholine, trimethylamine, triethylamine, tri-n-pentylamine, tri-n-hexylamine, triphenlyamine, pyridine, 1,8-diazabicyclo-[5,4,0]-7-undecene, hydrazine, trimethylenediamine, pentamethylenediamine, hexamethylenediamine, piperazine, m-phenylendiamine, 1,3-diazocyclohexane, triethylendiamine, N, N, N', N'-tetramethylethylenediamine, ammonia, urea, carbohydrazide, thiocarbohydrazide, azodicarbonamide, guanidine, dicyandiamide, aminoguanidine, N, N'-bis (3-aminopropyl) piperazine, melamine, acetoguanamine, 3-amino-1,2,4-tetrazole and hexamethylenetetramine.

* * * * *